(12) United States Patent
Rottenberg et al.

(10) Patent No.: US 9,668,766 B2
(45) Date of Patent: Jun. 6, 2017

(54) NEEDLE AND GUIDEWIRE HOLDER

(71) Applicant: The Spectranetics Corporation, Colorado Springs, CO (US)

(72) Inventors: Dan Rottenberg, Haifa (IL); Ronen Sacher, Herzelia (IL)

(73) Assignee: The Spectranetics Corporation, Colorado Springs, CO (US)

( * ) Notice: Subject to any disclaimer, the term of this patent is extended or adjusted under 35 U.S.C. 154(b) by 0 days.

(21) Appl. No.: 14/857,245

(22) Filed: Sep. 17, 2015

(65) Prior Publication Data

US 2016/0000454 A1 Jan. 7, 2016

Related U.S. Application Data

(63) Continuation of application No. 13/390,143, filed as application No. PCT/US2011/064301 on Dec. 12, 2011, now Pat. No. 9,162,038.

(Continued)

(51) Int. Cl.
*A61B 17/00* (2006.01)
*A61B 17/3207* (2006.01)
(Continued)

(52) U.S. Cl.
CPC .......... *A61B 17/3207* (2013.01); *A61B 17/22* (2013.01); *A61B 17/221* (2013.01); *A61M 25/0054* (2013.01); *A61M 25/065* (2013.01); *A61M 25/0606* (2013.01); *A61M 25/09041* (2013.01); *A61B 2017/00367* (2013.01); *A61B 2017/00477* (2013.01); *A61B 2017/22001* (2013.01); *A61B 2017/22035* (2013.01); *A61B 2017/22038* (2013.01); *A61B 2017/22069* (2013.01); *A61B 2017/22094* (2013.01); *A61B 2017/320052* (2013.01); *A61M 2025/09116* (2013.01); *A61M 2025/09125* (2013.01)

(58) Field of Classification Search
CPC ........ A61M 2025/09125; A61M 25/06; A61M 25/065; A61M 25/09041; A61B 5/150389; A61B 5/150213
See application file for complete search history.

(56) References Cited

U.S. PATENT DOCUMENTS 2,667,324 A 1/1954 Hansen
2,987,292 A 6/1961 Barkell et al.
(Continued)

FOREIGN PATENT DOCUMENTS

EP 0257811 A2 3/1988
EP 0342505 B1 11/1989
(Continued)

OTHER PUBLICATIONS

Merit Medical Systems, Inc. Merit Marquis Flow Switch: Traditional Premarket Notification 510(k). Section 510(k) summary, Jul. 1, 2011, 6 pages.
(Continued)

*Primary Examiner* — Scott Medway
(74) *Attorney, Agent, or Firm* — Faegre Baker Daniels LLP

(57) ABSTRACT

Device and method for puncturing blood vessels while using fluoroscopy. The disclosed device enables improved needle orientation control and avoids direct exposure of the clinician's hand to X-ray during the puncturing procedure.

15 Claims, 1 Drawing Sheet

US 9,668,766 B2

Page 2

Related U.S. Application Data

(60) Provisional application No. 61/626,183, filed on Sep. 22, 2011, provisional application No. 61/573,935, filed on Sep. 15, 2011, provisional application No. 61/575,160, filed on Aug. 17, 2011, provisional application No. 61/571,856, filed on Jul. 7, 2011, provisional application No. 61/516,906, filed on Apr. 11, 2011.

(51) Int. Cl.
*A61B 17/22* (2006.01)
*A61B 17/221* (2006.01)
*A61M 25/00* (2006.01)
*A61M 25/06* (2006.01)
*A61M 25/09* (2006.01)
*A61B 17/32* (2006.01)

(56) References Cited

U.S. PATENT DOCUMENTS

| | | |
|---|---|---|
| 3,585,996 A | 6/1971 | Pannier et al. |
| 3,859,998 A * | 1/1975 | Thomas et al. ......... 604/168.01 |
| RE28,713 E * | 2/1976 | Stevens et al. ............. 604/240 |
| 4,013,080 A | 3/1977 | Froning |
| 4,143,853 A | 3/1979 | Abramson |
| 4,200,096 A * | 4/1980 | Charvin .................. 604/170.01 |
| 4,243,034 A | 1/1981 | Brandt |
| 4,264,020 A | 4/1981 | Loiseau |
| 4,269,186 A * | 5/1981 | Loveless et al. ........ 604/168.01 |
| 4,274,408 A | 6/1981 | Nimrod |
| 4,333,455 A | 6/1982 | Bodicky |
| 4,417,886 A | 11/1983 | Frankhouser et al. |
| 4,468,224 A | 8/1984 | Enzmann et al. |
| 4,525,157 A | 6/1985 | Vaillancourt |
| 4,540,411 A | 9/1985 | Bodicky |
| 4,564,011 A | 1/1986 | Goldman |
| 4,641,912 A | 2/1987 | Goldenberg |
| 4,654,031 A * | 3/1987 | Lentz ..................... 604/168.01 |
| 4,655,750 A | 4/1987 | Vaillancourt |
| 4,768,709 A | 9/1988 | Yie |
| 4,789,104 A | 12/1988 | Anderson |
| 4,842,591 A | 6/1989 | Luther |
| 4,857,062 A | 8/1989 | Russell |
| 4,860,742 A | 8/1989 | Park et al. |
| 4,863,431 A | 9/1989 | Vaillancourt |
| 4,890,742 A | 1/1990 | Allison |
| 4,924,863 A | 5/1990 | Sterzer |
| 4,966,588 A | 10/1990 | Rayman et al. |
| 4,973,329 A | 11/1990 | Park et al. |
| 4,978,341 A | 12/1990 | Niederhauser |
| 5,007,901 A | 4/1991 | Shields |
| 5,011,472 A | 4/1991 | Aebischer et al. |
| 5,011,473 A | 4/1991 | Gatturna |
| 5,045,065 A | 9/1991 | Raulerson |
| 5,053,013 A | 10/1991 | Ensminger et al. |
| 5,066,284 A * | 11/1991 | Mersch et al. .......... 604/168.01 |
| 5,085,645 A | 2/1992 | Purdy et al. |
| 5,098,396 A | 3/1992 | Taylor et al. |
| 5,116,323 A | 5/1992 | Kreuzer et al. |
| 5,125,903 A | 6/1992 | McLaughlin et al. |
| 5,129,884 A | 7/1992 | Dysarz |
| 5,159,861 A | 11/1992 | Anderson |
| 5,178,153 A | 1/1993 | Einzig |
| 5,179,861 A | 1/1993 | Asano et al. |
| 5,195,978 A | 3/1993 | Schiffer |
| 5,226,879 A | 7/1993 | Ensminger et al. |
| 5,242,414 A * | 9/1993 | Fischell et al. .......... 604/168.01 |
| 5,273,042 A | 12/1993 | Lynch et al. |
| 5,281,199 A | 1/1994 | Ensminger et al. |
| 5,295,969 A | 3/1994 | Fischell et al. |
| 5,295,970 A * | 3/1994 | Clinton et al. .......... 604/168.01 |
| 5,308,318 A | 5/1994 | Plassche et al. |
| 5,325,746 A | 7/1994 | Anderson |
| 5,334,187 A | 8/1994 | Fischell et al. |
| 5,366,441 A | 11/1994 | Crawford |
| 5,395,348 A | 3/1995 | Ryan |
| 5,397,310 A | 3/1995 | Chu et al. |
| 5,417,699 A | 5/1995 | Klein et al. |
| 5,456,284 A | 10/1995 | Ryan et al. |
| 5,468,239 A | 11/1995 | Tanner et al. |
| 5,489,274 A | 2/1996 | Chu et al. |
| 5,497,782 A | 3/1996 | Fugoso |
| 5,501,227 A | 3/1996 | Yock |
| 5,501,671 A | 3/1996 | Rosen et al. |
| 5,520,665 A | 5/1996 | Fleetwood |
| 5,537,499 A | 7/1996 | Brekke |
| 5,540,236 A | 7/1996 | Ginn |
| 5,573,516 A | 11/1996 | Tyner |
| 5,573,531 A | 11/1996 | Gregory |
| 5,613,663 A | 3/1997 | Schmidt et al. |
| 5,685,862 A | 11/1997 | Mahurkar |
| 5,702,367 A | 12/1997 | Cover et al. |
| 5,704,914 A | 1/1998 | Stocking et al. |
| 5,749,861 A | 5/1998 | Guala et al. |
| 5,820,596 A | 10/1998 | Rosen et al. |
| 5,827,234 A * | 10/1998 | Loos et al. .................... 604/236 |
| 5,843,046 A | 12/1998 | Motisi et al. |
| RE36,104 E | 2/1999 | Solar |
| 5,879,338 A | 3/1999 | Mahurkar |
| 5,921,970 A | 7/1999 | Vandenberg |
| 5,980,492 A | 11/1999 | Rosen et al. |
| 5,984,895 A | 11/1999 | Padilla et al. |
| 5,989,223 A | 11/1999 | Chu et al. |
| 6,007,522 A | 12/1999 | Agro et al. |
| 6,096,009 A | 8/2000 | Windheuser et al. |
| 6,152,910 A | 11/2000 | Agro et al. |
| 6,165,215 A | 12/2000 | Rottenberg et al. |
| 6,176,852 B1 | 1/2001 | Ischinger |
| 6,182,463 B1 | 2/2001 | Strussion et al. |
| 6,196,230 B1 | 3/2001 | Hall et al. |
| 6,197,001 B1 | 3/2001 | Wilson et al. |
| 6,235,001 B1 | 5/2001 | O'Holloran et al. |
| 6,277,100 B1 * | 8/2001 | Raulerson et al. ............ 604/212 |
| 6,287,280 B1 | 9/2001 | Lampropoulos et al. |
| 6,312,404 B1 | 11/2001 | Agro et al. |
| 6,315,753 B1 * | 11/2001 | Cragg et al. .................... 604/15 |
| 6,346,093 B1 | 2/2002 | Allman et al. |
| 6,488,667 B1 | 12/2002 | Murphy |
| 6,488,674 B2 | 12/2002 | Becker et al. |
| 6,520,951 B1 | 2/2003 | Carrillo et al. |
| 6,524,277 B1 * | 2/2003 | Chang ...................... 604/164.02 |
| 6,572,590 B1 | 6/2003 | Stevens et al. |
| 6,572,791 B2 | 6/2003 | Sakata et al. |
| 6,582,401 B1 | 6/2003 | Windheuser et al. |
| 6,606,515 B1 | 8/2003 | Windheuser et al. |
| 6,663,597 B1 | 12/2003 | Windheuser et al. |
| 6,694,983 B2 | 2/2004 | Wolf et al. |
| 6,746,442 B2 | 6/2004 | Agro et al. |
| 6,808,498 B2 | 10/2004 | Laroya et al. |
| 6,869,416 B2 | 3/2005 | Windheuser et al. |
| 6,879,854 B2 | 4/2005 | Windheuser et al. |
| 6,997,908 B2 | 2/2006 | Carrillo et al. |
| 7,008,404 B2 | 3/2006 | Nakajima |
| 7,025,746 B2 * | 4/2006 | Tal ............................. 604/164.1 |
| 7,060,052 B2 | 6/2006 | Windheuser et al. |
| 7,076,285 B2 | 7/2006 | Windheuser et al. |
| 7,172,577 B2 | 2/2007 | Mangano et al. |
| 7,179,252 B2 | 2/2007 | Agro et al. |
| 7,241,285 B1 | 7/2007 | Dikeman |
| 7,261,703 B2 | 8/2007 | Lampropoulos et al. |
| 7,355,182 B2 | 4/2008 | Szu |
| 7,396,343 B2 | 7/2008 | Brown |
| 7,544,184 B2 | 6/2009 | Cope et al. |
| 7,544,193 B2 | 6/2009 | Agro et al. |
| 7,578,814 B2 | 8/2009 | Accisano et al. |
| 7,615,033 B2 | 11/2009 | Leong |
| 7,678,129 B1 | 3/2010 | Gesswein et al. |
| 7,682,340 B2 | 3/2010 | Funamura et al. |
| 7,706,861 B2 | 4/2010 | Windheuser et al. |
| 7,708,721 B2 | 5/2010 | Khaw |
| 7,722,567 B2 | 5/2010 | Tal |
| 7,760,316 B2 | 7/2010 | Hirakata et al. |
| 7,819,844 B2 | 10/2010 | Spenser et al. |

(56) References Cited

U.S. PATENT DOCUMENTS

| | | |
|---|---|---|
| 7,846,133 B2 | 12/2010 | Windheuser et al. |
| 7,909,811 B2 | 3/2011 | Agro et al. |
| 7,918,859 B2 | 4/2011 | Katoh et al. |
| 8,006,953 B2 | 8/2011 | Bennett |
| 8,043,208 B2 | 10/2011 | Windheuser et al. |
| 8,052,647 B2 | 11/2011 | Raulerson et al. |
| 8,066,669 B2 | 11/2011 | Christensen et al. |
| 8,066,670 B2 | 11/2011 | Cluff et al. |
| 8,066,679 B2 | 11/2011 | Hwang |
| 8,083,690 B2 | 12/2011 | Peterson et al. |
| 8,105,286 B2 | 1/2012 | Anderson et al. |
| 8,128,598 B2 | 3/2012 | Uihlein |
| 8,177,760 B2 | 5/2012 | Rome et al. |
| 8,192,402 B2 * | 6/2012 | Anderson et al. ......... 604/164.1 |
| 8,202,251 B2 | 6/2012 | Bierman et al. |
| 8,202,254 B2 | 6/2012 | Schweikert et al. |
| 8,206,283 B2 | 6/2012 | Windheuser et al. |
| 8,206,375 B2 | 6/2012 | Snow |
| 8,211,087 B2 | 7/2012 | Carter et al. |
| 8,216,295 B2 | 7/2012 | Benjamin et al. |
| 8,257,382 B2 | 9/2012 | Rottenberg et al. |
| 8,257,383 B2 | 9/2012 | Rottenberg et al. |
| 8,597,252 B2 * | 12/2013 | Burkholz et al. ......... 604/168.01 |
| 9,289,173 B2 | 3/2016 | Splinter |
| 2002/0026188 A1 | 2/2002 | Balbierz et al. |
| 2002/0068885 A1 | 6/2002 | Harhen et al. |
| 2004/0122416 A1 * | 6/2004 | Schweikert et al. .......... 604/528 |
| 2004/0131299 A1 | 7/2004 | Adoram et al. |
| 2004/0215146 A1 | 10/2004 | Lampropoulos et al. |
| 2005/0143770 A1 | 6/2005 | Carter et al. |
| 2005/0148925 A1 | 7/2005 | Rottenberg et al. |
| 2005/0159770 A1 | 7/2005 | Divani et al. |
| 2005/0245885 A1 | 11/2005 | Brown |
| 2006/0020241 A1 | 1/2006 | Piskun et al. |
| 2006/0264834 A1 | 11/2006 | Vaillancourt |
| 2007/0118079 A1 | 5/2007 | Moberg et al. |
| 2007/0162071 A1 | 7/2007 | Burkett et al. |
| 2008/0159825 A1 | 7/2008 | Tegg |
| 2008/0234567 A1 | 9/2008 | Tearney et al. |
| 2008/0243065 A1 | 10/2008 | Rottenberg et al. |
| 2008/0243067 A1 | 10/2008 | Rottenberg et al. |
| 2008/0300574 A1 | 12/2008 | Belson et al. |
| 2008/0300662 A1 | 12/2008 | Taylor |
| 2009/0005754 A1 | 1/2009 | Soetermans |
| 2009/0221961 A1 | 9/2009 | Tal et al. |
| 2009/0254074 A1 | 10/2009 | Splinter et al. |
| 2009/0292253 A1 | 11/2009 | Raulerson et al. |
| 2010/0094310 A1 | 4/2010 | Warring et al. |
| 2011/0021994 A1 * | 1/2011 | Anderson et al. ....... 604/164.01 |
| 2011/0060315 A1 | 3/2011 | Windheuser et al. |
| 2011/0077621 A1 | 3/2011 | Graham et al. |
| 2011/0144572 A1 | 6/2011 | Kassab et al. |
| 2011/0196344 A1 | 8/2011 | Agro et al. |
| 2011/0251559 A1 | 10/2011 | Tal et al. |
| 2011/0270192 A1 | 11/2011 | Anderson et al. |
| 2011/0276002 A1 | 11/2011 | Bierman |
| 2011/0282285 A1 | 11/2011 | Blanchard et al. |
| 2012/0041371 A1 | 2/2012 | Tal et al. |
| 2012/0184896 A1 | 7/2012 | DeLegge et al. |
| 2012/0220942 A1 | 8/2012 | Hall et al. |
| 2012/0265229 A1 | 10/2012 | Rottenberg et al. |
| 2012/0265233 A1 | 10/2012 | Waisman et al. |
| 2013/0165867 A1 | 6/2013 | Isaacson et al. |
| 2015/0148790 A1 | 5/2015 | Fix |
| 2015/0245796 A1 | 9/2015 | Splinter |
| 2016/0183844 A1 | 6/2016 | Splinter |

FOREIGN PATENT DOCUMENTS

| | | |
|---|---|---|
| EP | 0388112 B1 | 9/1990 |
| EP | 0583049 A1 | 2/1994 |
| EP | 0623673 A2 | 11/1994 |
| EP | 0633184 A1 | 1/1995 |
| EP | 0650666 A1 | 5/1995 |
| EP | 0724098 A1 | 7/1996 |
| EP | 0846064 A1 | 6/1998 |
| EP | 0897295 A1 | 2/1999 |
| EP | 0922466 B1 | 6/1999 |
| EP | 1035880 A1 | 9/2000 |
| EP | 1045708 A1 | 10/2000 |
| EP | 1098671 A1 | 5/2001 |
| EP | 1109590 A1 | 6/2001 |
| EP | 1399549 A1 | 3/2004 |
| EP | 1441672 A1 | 8/2004 |
| EP | 1546664 A1 | 6/2005 |
| EP | 1771132 A2 | 4/2007 |
| EP | 1789122 A2 | 5/2007 |
| EP | 2052756 B1 | 4/2009 |
| EP | 2055266 A2 | 5/2009 |
| EP | 2012660 B1 | 9/2009 |
| EP | 2131913 A1 | 12/2009 |
| EP | 2163216 A2 | 3/2010 |
| EP | 2163217 A2 | 3/2010 |
| EP | 2185107 A1 | 5/2010 |
| EP | 2470248 | 3/2011 |
| EP | 2399550 A1 | 12/2011 |
| EP | 2473123 A1 | 7/2012 |
| EP | 2494419 A2 | 9/2012 |
| EP | 2512577 A2 | 10/2012 |
| EP | 1796597 B1 | 1/2013 |
| WO | WO8809188 A | 12/1988 |
| WO | WO9306878 A | 4/1993 |
| WO | WO9706973 A | 2/1997 |
| WO | WO9828034 A | 7/1998 |
| WO | 9926677 A1 | 6/1999 |
| WO | 0003754 A1 | 1/2000 |
| WO | 0013736 A1 | 3/2000 |
| WO | 0037128 A1 | 6/2000 |
| WO | 02070061 A1 | 9/2002 |
| WO | 03002182 A1 | 1/2003 |
| WO | 03002734 A1 | 1/2003 |
| WO | WO03047468 A1 | 6/2003 |
| WO | 2004025229 A1 | 3/2004 |
| WO | 2005011792 A1 | 2/2005 |
| WO | 2005028002 A1 | 3/2005 |
| WO | 2006019592 A2 | 2/2006 |
| WO | 2008035349 A1 | 3/2008 |
| WO | 2008120209 A1 | 10/2008 |
| WO | 2009033173 A1 | 3/2009 |
| WO | 2009132027 A1 | 10/2009 |
| WO | 2010091356 A1 | 8/2010 |
| WO | 2010137024 A1 | 12/2010 |
| WO | 2011025855 A2 | 3/2011 |
| WO | 2011028632 A1 | 3/2011 |
| WO | 2011041578 A2 | 4/2011 |
| WO | 2011084616 A2 | 7/2011 |
| WO | 2011051944 A8 | 3/2012 |
| WO | 2012141748 A1 | 10/2012 |

OTHER PUBLICATIONS

MeritMedical Flow Control Switch—Instructions for Use. Merit Medical Systems, Inc. 2 pages.
MeritMedical: Flow Control Switch Confidently Control Fluid Flow. Merit Medical Systems, Inc. 2 pages.
NAMIC@ Fluid Management: Constructed for Confidence. Configured for Care. Systems for Cardiac Catheterization Labs. Navilyst Medical, Inc. 2009, 11 pages.
Office Action for U.S. Appl. No. 12/061,430 mailed Dec. 19, 2018, 10 pages.
Office Action for U.S. Appl. No. 12/176,886 mailed Jan. 25, 2013, 10 pages.
Office Action for U.S. Appl. No. 12/176,886 mailed Sep. 26, 2012, 12 pages.
Product Catalogue: Peripheral Interventions Vascular Surgery, Boston Scientific, 147 pages.
Qosina Part No. 97337 (Inline Flow Control Switch). Dec. 1, 2012, 1 page.

(56) References Cited

OTHER PUBLICATIONS

International Search Report issued in PCT/US2011/064301, mailed May 25, 2012, 3 pages.

* cited by examiner

NEEDLE AND GUIDEWIRE HOLDER

CROSS REFERENCE TO RELATED APPLICATIONS

The present application is a continuation of prior U.S. application Ser. No. 13/390,143, filed Feb 13, 2012, entitled "NEEDLE AND GUIDEWIRE HOLDER," which is the United States national phase of International Application No. PCT/US11/64301 filed Dec 12, 2011 entitled "NEEDLE AND GUIDEWIRE HOLDER," which claims the benefit of and priority to, under 35 U.S.C. §119(e) and/or 120, U.S. Provisional Application Ser. No. 61/516,906 filed Apr 11, 2011 entitled "DEVICE AND METHOD FOR BTK BLOOD VESSEL TREATMENT," and U.S. Provisional Application Ser. No. 61/571,856 filed Jul 7, 2011 entitled "NEEDLE-HOLDER FOR BLOOD VESSELS PUNCTURE," and U.S. Provisional Application Ser. No. 61/575,160 filed Aug 17, 2011 entitled "DEVICE AND METHOD FOR GUIDEWIRES CAPTURING," and U.S. Provisional Application Ser. No. 61/573,935 filed Sep 15, 2011 entitled "NEEDLE-HOLDER WITH INTEGRATED GUIDEWIRE HOLDER FOR BLOOD VESSELS PUNCTURE," and U.S. Provisional Application Ser. No. 61/626,183 filed Sep 22, 2011 entitled "HYPO-TUBE BASED SUPPORT CATHETER," each of which is hereby incorporated herein by reference in its entirety for all that it teaches and for all purposes.

FIELD OF THE INVENTION

The present invention generally relates to a device and a method for needle puncturing of small blood vessels for small vessel angioplasty, such as below the knee (BTK) blood vessels and other small blood vessels (e.g., coronary, pediatric), which are partially or totally occluded.

BACKGROUND OF THE INVENTION

A chronic total occlusion (CTO) is an arterial vessel blockage that prevents blood flow beyond the obstruction. CTO's typically occur in coronary, peripheral, pediatric, and other small arteries. In the coronary and peripheral arteries, they result from the same underlying cause—atherosclerosis.

Endovascular therapies for arteries below the knee have emerged as a promising revascularization technique for patients with critical limb ischemia (CLI). However, when employing standard angioplasty techniques, angioplasty of BTK arteries fails to achieve revascularization in up to 20% of cases. The main cause for failure is the inability to penetrate the plaque's proximal cap with the guidewire.

A new technique of approaching the plaque from below—known as the retrograde approach—is often used to pass the guidewire through the plaque from the other direction. This approach has high success rates, but is technically challenging to perform and has its own complications, especially the danger of vessel perforation.

In order to use the retrograde technique, the clinician must puncture the small target artery with a needle—usually smaller than a 21 gauge needle. The clinician relies on several angiographic images to aim the needle into the artery, and verifies proper needle tip location by observing blood flow exiting from the needle's proximal end.

Puncturing small arteries is not easy; it requires proper manipulation of the C-arm and a gentle needle stick to avoid arterial perforation. Once a guidewire is inserted (through a small sheath or directly (sheath-less) through the skin) within the needle into the artery, the needle can be removed.

Currently, relative short standard needles are used to puncture small blood vessels. Long needles that might potentially extend the user hand from the puncturing site are not used for two reasons:

1) Long thin needles are too flexible, which prevents accurate and controlled positioning of the needle tip in the direction of the blood vessel; and 2) Blood is expected to come out from the proximal end of the needle. This is fine for a short needle, but for a long needle the blood may not reach the proximal end due to low blood pressure in the treated vessel and high flow resistance of the long narrow needle lumen.

Another important disadvantage of the prior art, is that during this needle insertion the clinician's hand is exposed to direct X-ray radiation which may have deleterious long-term health effects.

SUMMARY OF THE INVENTION

The present invention is directed to a device and a method for needle puncturing of blood vessels for vessel angioplasty. The invention seeks to provide a special needle holder that facilitates needle insertion, and increases the needle puncturing procedure accuracy, while preventing hand exposure to radiation.

In accordance with an embodiment of the invention, a standard needle is affixed onto a special extended needle holder, e.g., by using a female to male standard luer connection. The needle holder reduces the clinician's hand exposure to x-rays during the needle insertion and provides better control of the needle trajectory and puncture. The device includes a vent for both blood passage to confirm needle tip location in the target artery and for guidewire passage. A standard guidewire may be inserted through the needle into the artery. Afterwards, the needle and needle holder are removed.

Optionally, a guidewire holding mechanism is provided that reduces procedure time and minimizes blood spillage, by holding the distal portion of the guidewire inside the needle holder.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
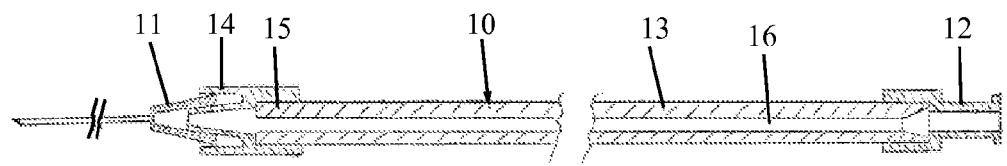
FIG. 1 is a simplified cross-sectional illustration of a needle holder, in accordance with an embodiment of the present invention.

Reference is now made to FIG. 1, which illustrates a needle holder 10, constructed and operative in accordance with an embodiment of the present invention.

Needle holder 10 is an elongate stiff member 13 that includes a needle connector 14, such as but not limited to, a male luer connector, at a distal end 15 thereof. Connector 14 connects to a needle 11, such as by means of connecting with a female luer connector affixed to the proximal end of the needle 11. Needle holder 10 may be supplied without the needle 11 and the user connects the holder to the needle.

Alternatively, needle holder 10 may be supplied with needle 11 already assembled therewith. Without limitation, needle holder 10 preferably has a length of at least 12 cm, most preferably in the range of 20-25 cm; holder 10 is preferably longer than the needle 11. The elongate stiff member 13 may be a hollow tube with a lumen 16, which may be made, without limitation, from a stiff, clear polymeric material, e.g., polycarbonate. Lumen 16 is big enough for easy blood flow therethrough, preferably, but not necessarily, having a diameter of equal to or more than 1.0 mm The long and stiff holder 10 reduces the clinician's hand exposure to x-rays during insertion of needle 11, and provides better control of the needle orientation, trajectory, and puncture.

Needle holder 10 includes a vent 12 at a proximal end thereof for blood flow to verify that the needle tip is properly located inside the blood vessel. Vent 12 preferably, but not necessarily, has a standard female luer shape.

Figure 2:
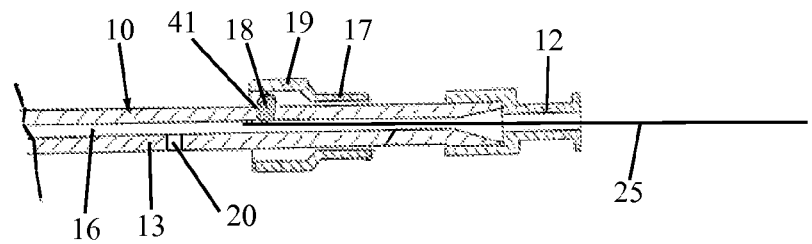
FIG. 2 is a simplified cross-sectional illustration of a needle holder with a guidewire holder, in accordance with an embodiment of the present invention.

Reference is now made to FIG. 2, which illustrates a needle holder 10 and guidewire holder 17, constructed and operative in accordance with an embodiment of the present invention.

Guidewire holder 17 may be used to hold the distal portion of a guidewire 25 inside the needle holder lumen before and during blood vessel puncturing. The option to hold the guidewire distal section inside the needle holder lumen may be useful for the operator, because it eliminates the need to look for the guidewire at the operation table, while holding the needle and needle holder steady. It reduces the amount of blood coming out of the needle, and spillage near the patient, by shortening the time needed to insert the guidewire through the needle.

Guidewire holder 17 includes a guidewire locking element 18, which may be made of a flexible material, such as but not limited to, silicone. A sliding knob 19 is arranged to slide over guidewire locking element 18, which forces element 18 through a small hole 41 in elongate stiff member 13 into lumen 16, thereby pressing the distal end of guidewire 25 against the inner wall of lumen 16 and holding guidewire 25 in place. To release guidewire 25, the user slides sliding knob 19 to release guidewire locking element 18 from lumen 16.

A vent hole 20 may be added to elongate stiff member 13 distal to guidewire holder 17 to allow free blood flow outwards from the needle, even if lumen 16 is blocked by guidewire holder closing element 18.

Guidewire locking element 18 and/or other locking elements can be alternatively assembled to vent 12.

In accordance with an embodiment of the present invention, the procedure steps are:

a. Fix needle 11 into connector 14.
b. Optionally insert and lock the distal portion of guidewire 25 inside needle holder lumen 16.
c. Using x-ray angiography, insert and adjust the needle and needle tip until entering the blood vessel.
d. Confirm needle tip is inside the blood vessel by looking at blood coming up into lumen 16 of elongate stiff member 13.
e. Insert guidewire 25 through vent 12 (e.g., female luer) and lumen 16 (if not inserted and locked before), through connector 14 and needle 11, and into the blood vessel.
f. Extract needle holder 10 together with needle 11 from the patient, and remove proximally from guidewire 25.
g. Continue the angioplasty procedure.

What is claimed is:

1. A method comprising:
    connecting a needle to a needle holder, the needle holder comprising:
        an elongate stiff member having a proximal end, a distal end, and a longitudinal axis;
        a connector coupled to the distal end of the elongate stiff member;
        a guidewire holder coupled to the elongate stiff member proximally of the distal end, the guidewire holder comprising:
            (a) a flexible locking element located proximally of the distal end of the elongate stiff member;
            (b) a sliding knob arranged to slide over the locking element in a direction parallel to the longitudinal axis and force the flexible locking element in a radial direction;
        a lumen traversing the connector, the elongate stiff member, and the guidewire holder, wherein the lumen comprises an inner wall and an opening disposed proximally of the locking element;
    inserting the needle into a blood vessel;
    inserting a guidewire into the blood vessel through the lumen and the needle;
    sliding the sliding knob over the flexible locking element to cause the flexible locking element to directly contact and press the guidewire against the inner wall and hold the guidewire in place.

2. The method according to claim 1, wherein inserting the needle into the blood vessel comprises using x-ray angiography.

3. The method according to claim 1, further comprising confirming that the needle is positioned in the blood vessel by viewing blood in the elongate stiff member.

4. The method according to claim 1, further comprising removing the needle holder together with the needle from the blood vessel.

5. The method according to claim 4, further comprising removing the needle holder and the needle proximally from the guidewire.

6. The method according to claim 5, further comprising conducting an angioplasty procedure after removing the needle holder and the needle proximally from the guidewire.

7. The method according to claim 1, further comprising conducting an angioplasty procedure after sliding the sliding knob over the flexible locking element.

8. The method according to claim 1, wherein the connector comprises a male luer connector.

9. The method according to claim 1, wherein the opening comprises a female luer connector.

10. The method according to claim 1, wherein the needle holder has a length of at least 12 cm.

11. The method according to claim 1, wherein the needle holder has a length of 20 cm to 25 cm.

12. The method according to claim 1, further comprising a second opening in fluid communication with the lumen.

13. The method according to claim 12, wherein the second opening is located distal to the flexible locking element and proximal of the distal end of the elongate stiff member.

14. The method according to claim 1, wherein the elongate stiff member is constructed of a clear polymeric material.

15. The method according to claim 1, wherein the flexible locking element is located within a hole within the elongate stiff member.

* * * * *

UNITED STATES PATENT AND TRADEMARK OFFICE
CERTIFICATE OF CORRECTION

PATENT NO. : 9,668,766 B2  
APPLICATION NO. : 14/857245  
DATED : June 6, 2017  
INVENTOR(S) : Rottenberg et al.

It is certified that error appears in the above-identified patent and that said Letters Patent is hereby corrected as shown below:

In the Specification

In Column 1, Line 7, delete "2012," and insert -- 2012, now Pat. No. 9,162,038, --, therefor.

In Column 1, Line 42, delete "CTO's" and insert -- CTOs --, therefor.

In Column 3, Line 10, delete "1.0 mm" and insert -- 1.0 mm. --, therefor.

Signed and Sealed this  
First Day of August, 2017

Joseph Matal  
*Performing the Functions and Duties of the*  
*Under Secretary of Commerce for Intellectual Property and*  
*Director of the United States Patent and Trademark Office*